US009920372B2

(12) United States Patent
Akirav

(10) Patent No.: US 9,920,372 B2
(45) **Date of Patent: *Mar. 20, 2018**

(54) METHOD FOR USING PROBE BASED PCR DETECTION TO MEASURE THE LEVELS OF CIRCULATING DEMETHYLATED BETA CELL DERIVED DNA AS A MEASURE OF BETA CELL LOSS IN DIABETES

(71) Applicant: Winthrop-University Hospital, Mineola, NY (US)

(72) Inventor: Eitan Moshe Akirav, Plainview, NY (US)

(73) Assignee: NYU Winthrop Hospital, Mineola, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,899

(22) Filed: Sep. 3, 2015

(65) Prior Publication Data

US 2015/0376706 A1 Dec. 31, 2015

Related U.S. Application Data

(63) Continuation of application No. 13/784,017, filed on Mar. 4, 2013, now Pat. No. 9,127,317, which is a continuation of application No. PCT/US2013/028862, filed on Mar. 4, 2013.

(60) Provisional application No. 61/606,140, filed on Mar. 2, 2012.

(51) Int. Cl.
*C12Q 1/68* (2006.01)

(52) U.S. Cl.
CPC ..... *C12Q 1/6883* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,935,342 | A | 6/1990 | Seligson et al. |
| 5,057,426 | A | 10/1991 | Henco et al. |
| 5,234,809 | A | 8/1993 | Boom et al. |
| 5,405,951 | A | 4/1995 | Woodard |
| 5,990,301 | A | 11/1999 | Colpan et al. |
| 6,020,124 | A | 2/2000 | Sorenson |
| 6,103,476 | A | 8/2000 | Tyagi et al. |
| 6,150,097 | A | 11/2000 | Tyagi et al. |
| 6,214,979 | B1 | 4/2001 | Gelfand et al. |
| 6,485,901 | B1 | 11/2002 | Gildea et al. |
| 6,485,903 | B1 | 11/2002 | Mayrand |
| 6,548,254 | B2 | 4/2003 | Beckman et al. |
| 6,649,349 | B2 | 11/2003 | Gildea et al. |
| 6,680,377 | B1 | 1/2004 | Stanton et al. |
| 6,811,973 | B1 | 11/2004 | Reich |
| 7,005,265 | B1 | 2/2006 | Fan et al. |
| 7,015,317 | B2 | 3/2006 | Mullen et al. |
| 7,070,933 | B2 | 7/2006 | Browne |
| 7,081,336 | B2 | 7/2006 | Bao et al. |
| 7,153,654 | B2 | 12/2006 | Wei et al. |
| 7,183,052 | B2 | 2/2007 | Sorge |
| 7,241,596 | B2 | 7/2007 | Mayrand |
| 7,271,265 | B2 | 9/2007 | Haugland et al. |
| 7,332,277 | B2 | 2/2008 | Dhallan |
| 7,399,591 | B2 | 7/2008 | Bao et al. |
| 7,413,708 | B2 | 8/2008 | Mayrand |
| 7,422,852 | B2 | 9/2008 | Gildea et al. |
| 7,442,506 | B2 | 10/2008 | Dhallan |
| 7,598,390 | B2 | 10/2009 | Bradford et al. |
| 7,619,059 | B2 | 11/2009 | Kupcho et al. |
| 7,632,642 | B2 | 12/2009 | Wangh et al. |
| 7,662,550 | B1 | 2/2010 | Tyagi et al. |
| 7,709,194 | B2 | 5/2010 | Lo et al. |
| 7,718,370 | B2 | 5/2010 | Dhallan |
| 7,727,720 | B2 | 6/2010 | Dhallan |
| 7,754,428 | B2 | 7/2010 | Lo et al. |
| 7,776,529 | B2 | 8/2010 | Dallwig et al. |
| 7,803,528 | B1 | 9/2010 | Chiang et al. |

(Continued)

FOREIGN PATENT DOCUMENTS

WO 2012097903 A1 7/2012

OTHER PUBLICATIONS

Akirav EM, Lebastchi J, Galvan EM, Henegariu 0, Akirav M, Ablamunits V, Lizardi PM, Herold KC. Detection of 13 cell death in diabetes using differentially methylated circulating DNA. Proc Natl Acad Sci US A. Nov. 22, 2011; 108(47):19018-23. Epub Nov. 9, 2011.*

Supporting Information for Akirav et al. (noted above). Proc Natl Acad Sci US A. Nov. 22, 2011; 108(47):19018-23. Epub Nov. 9, 2011.*

Campan M, Weisenberger DJ, Trinh B, Laird PW. Methylight. Methods Mol Biol. 2009; 507:325-37.*

Genbank Accession No. J00265.1—Human insulin gene, complete eds (GI: 186429, first submitted on Apr. 27, 1993 and updated Jan. 7, 2010, retrieved on Mar. 8, 2014 from http://www.ncbi.nlm.nih.gov/nuccore/J00265).*

Li LC, Dahiya R. Meth Primer: designing primers for methylation PC Rs. Bioinformatics. Nov. 2002; 18(11):1427-31.*

Trinh BN, Long TI, Laird PW. DNA methylation analysis by MethyLight technology. Methods. Dec. 2001; 25(4):456-62.*

Supplementary European Search Report for Application No. EP 13754517 dated Dec. 21, 2015.

(Continued)

*Primary Examiner* — Angela M Bertagna
*Assistant Examiner* — Olayinka Oyeyemi
(74) *Attorney, Agent, or Firm* — Amster, Rothstein & Ebenstein LLP

(57) ABSTRACT

A method for measuring blood levels of β cell DNA that is released upon β cell death by using a quantitative probe technology to detect amplified methylated and demethylated forms of the insulin gene DNA, representing normal tissue and β cell specific origin, respectively. Using probes permits the sensitive and specific identification of demethylated insulin DNA patterns that are present only in β cells. The method offers a bioassay for detecting β cell loss in diabetes, useful for screening of prediabetes, monitoring of disease progression, and selection and monitoring of therapies. The (Continued)

technique finds potential use in both Type I and Type II diabetes, as well as gestational diabetes.

11 Claims, 5 Drawing Sheets

(56) References Cited

U.S. PATENT DOCUMENTS 7,842,811 B2 11/2010 Dallwig et al.
7,847,076 B2 12/2010 Mayrand
7,892,741 B2 2/2011 Gildea et al.
7,901,884 B2 3/2011 Lo et al.
7,968,289 B2 6/2011 Coull et al.
7,972,786 B2 7/2011 Hartshorn et al.
8,026,067 B2 9/2011 Lo et al.
8,071,734 B2 12/2011 Stanton et al.
8,093,003 B2 1/2012 Chiang et al.
8,133,984 B2 3/2012 Christensen
8,211,644 B2 7/2012 Hanna et al.
8,247,171 B2 8/2012 Nurmi et al.
8,288,100 B2 10/2012 Lo et al.
8,476,013 B2 7/2013 Ehrich et al.
8,688,388 B2 4/2014 Dzakula et al.
8,748,100 B2 6/2014 Lo et al.
8,771,948 B2 7/2014 Wisniewski et al.
8,927,216 B2 1/2015 Lo et al.
8,962,247 B2 2/2015 Ehrich et al.
9,074,013 B2 7/2015 Rehli
9,075,063 B2 7/2015 Sakai et al.
9,127,317 B2 * 9/2015 Akirav ................ C12Q 1/6883
2002/0177127 A1 * 11/2002 Yang ...................... C12Q 1/703 435/5
2003/0143606 A1 7/2003 Olek et al.
2004/0171046 A1 9/2004 Berlin et al.
2004/0181048 A1 9/2004 Wang
2005/0250092 A1 * 11/2005 Jeney ..................... C12Q 1/708 435/5
2006/0134663 A1 6/2006 Harkin et al.
2007/0015156 A1 1/2007 Goggins et al.
2007/0043216 A1 2/2007 Bair, Jr. et al.
2007/0141582 A1 * 6/2007 Li ........................ C12Q 1/6886 435/6.12
2007/0212761 A1 * 9/2007 Sorge ................... C12Q 1/6816 435/91.2
2007/0231797 A1 10/2007 Fan et al.
2008/0034453 A1 2/2008 Cheikh et al.
2014/0256574 A1 9/2014 Herold et al.

OTHER PUBLICATIONS

Akirav E, Kushner JA, Herold Kc (2008) β-cell mass and type 1 diabetes: Going, going, gone? Diabetes 57:2883-2888.

Bluestone JA, Herold K, Eisenbarth G (2010) Genetics, pathogenesis and clinical interventions in type 1 diabetes. Mature 464:1293-1300.

Waldron-Lynch F, Herold KC (2009) Advances in type 1 diabetes therapeutics: Immunomodulation and β-cell salvage. Endocrinol Metab Clin North Am 38:303-317.

Bougneres PF, et al. (1988) Factors associated with early remission of type I diabetes in children treated with cyclosporine. N Engl J Med 318:663-670.

Keymeulen B, et al. (2005) Insulin needs after CD3-antibody therapy in new-onset type 1 diabetes. N Engl J Med 352:2598-2608.

Akirav, Eitan M. (2011) Detection of Beta Cell Death in Diabetes Using Differentially Methylated Circulating DNA, PNAA Early Edition and Supplemental.

Snorgaard O, Lassen LH, Binder C (1992) Homogeneity in pattern of decline of β-cell function in IDDM: Prospective study of 204 consecutive cases followed for 7.4 yr. Diabetes Care 15:1009-1013.

Greenbaum CJ, et al.; Type 1 Diabetes Trial Net Research Group; European C-Peptide Trial Study Group (2008) Mixed-meal tolerance test versus glucagon stimulation test for the assessment of β-cell function in therapeutic trials in type 1 diabetes. Diabetes Care 31:1966-1971.

Steele C, et al. (2004) Insulin secretion in type 1 diabetes. Diabetes 53:426-433.

Erlich H, et al.; Type 1 Diabetes Genetics Consortium (2008) HLA DR-DQ haplotypes and genotypes and type 1 diabetes risk: Analysis of the Type 1 Diabetes Genetics Consortium families. Diabetes 57:1084-1092.

Hagopian WA, et al. (1995) Glutamate decarboxylase, insulin, and islet cell antibodies and HLA typing to detect diabetes in a general population-based study of Swedish children. J Clin Invest 95:1505-1511.

Verge CF, et al. (1996) Prediction of type I diabetes in first-degree rel. Diabetes 45: 926-933.

Dhawan et al., Pancreatic Beta Cell Identity is Maintained by DNA Methylation-Mediated Repression of Arx, Developmental Cell, 20:419-429, Apr. 19, 2011.

Sosenko JM, et al.; Diabetes Prevention Trial Type 1 Study Group (2007) Increasing the accuracy of oral glucose tolerance testing and extending its application to individuals with normal glucose tolerance for the prediction of type 1 diabetes: The Diabetes Prevention Trial Type 1. Diabetes Care 30:38-42.

Medarova Z, Tsai S, Evgenov N, Santamaria P, Moore A (2008) In vivo imaging of a diabetogenic CD8+ T cell response during type 1 diabetes progression. Magn Reson Med 59:712-720.

Klose RJ, Bird AP (2006) Genomic DNA methylation: The mark and its mediators. Trends Biochem Sci 31:89-97.

Bartke T, et al. (2010) Nucleosome-interacting proteins regulated by DNA and histone methylation. Cell 143:470-484.

Wang GG, Allis CD, Chi P (2007) Chromatin remodeling and cancer, part II: ATP-dependent chromatin remodeling. Trends Mol Med 13:373-380.

Miranda TB, Jones PA (2007) DNA methylation: The nuts and bolts of repression. J Cell Physiol 213:384-390.

Grady WM, Rajput A, Lutterbaugh JD, Markowitz SD (2001) Detection of aberrantly methylated hMLH1 promoter DNA in the serum of patients with microsatellite un-stable colon cancer. Cancer Res 61:900-902.

Wallner M, et al. (2006) Methylation of serum DNA is an independent prognostic marker in colorectal cancer. Clin , Cancer Res 12:7347-7352.

Müller HM, et al. (2003) DNA methylation in serum of breast cancer patients: An independent prognostic marker. Cancer Res 63:7641-7645.

Poitout V, et al. (1995) Morphological and functional characterization of β TC-6 cells: An insulin-secreting cell line derived from transgenic mice. Diabetes 44:306-313.

Sherry NA, et al. (2006) Effects of autoimmunity and immune therapy on β-cell turnover in type 1 diabetes. Diabetes 55:3238-3245.

Jayaraman S (2011) Assessment of beta cell viability. Curr Protoc Cytom 55:6.27.1-627.16.

Kuroda A, et al. (2009) Insulin gene expression is regulated by DNA methylation. PLoS One 4:e6953.

Levenson, DNA Methylation as a Universal Biomarker, Expert Rev Mol Diagn., 10(4):481-488, May 2010.

Leiter EH, et al (2007) Unexpected functional consequences of xenogeneic transgene expression in β-cells of NOD mice. Diabetes Obes Metab 9(Suppl 2):14-22.

Trudeau JD, et al. (2000) Neonatal β-cell apoptosis: A trigger for autoimmune diabetes? Diabetes 49:1-7.

Fujimoto K, et al. (2010) Loss of Nix in Pdx1-deficient mice prevents apoptotic and necrotic β cell death and diabetes. J Clin Invest 120:4031-4039.

Volkmar et al, DNA Methylation Profiling Identifies Epigenetic Dysregulation in Pancreatic Islets from Type 2 Diabetic Patients, The EMBO Journal , 31:1405-1426, 2012.

Berney T, et al. (2006) Detection of insulin mRNA in the peripheral blood after human islet transplantion predicts deterioration of metabolic control. Am J Transplant 6:1704-1711.

Best CH, Haist RE, Ridout JH (1939) Diet and the insulin content of pancreas. J Physiol 97:107-119.

Collins TJ (2007) ImageJ for microscopy. Biotechniques 43(Suppl 1):25-30.

(56) References Cited

OTHER PUBLICATIONS

Yang, B.T. (2011) Insulin Promoter DNA Methylation Correlates Negatively with Insulin Gene Expression and Positively with HbA1C Levels in Human Pancreatic Islets, Diabetologia 54:360-367.
Husseiny et al, Development of a Quantitative Methylation-specific Polymerase Chain Reaction Method for Monitoring Beta Cell Death in Type 1 Diabetes, PloS One, Oct. 29, 2012, vol. 7, No. 10, pp. 1-11.
Darst, Russell P. (2010) Bisulfite Sequencing of DNA, Cuff Protoc Mol Biol.; Chapter: Unit 7.917.
Ley, Timothy J. (1984) DNA Methylation and Regulation of the Human Beta-Globin-Like Genes in Mouse Erythroleukemia Cells Containing Human Chromosome 11, Proc. Natl. Acad. Sci. USA, vol. 81, pp. 6618-6622.
Akirav et al, Detection of Beta Cell Death in Diabetes Using Differentially Methylated Circulating DNA, Proc Nat Acad Sci, Nov. 22, 2011, vol. 108, No. 47, pp. 19018-19023.
Bibikova et al, Genome-Wide DNA Methylation Profiling Using Infinium Assay, Epigenomics, Oct. 2009, vol. 1, No. 1, pp. 177-200.
Kutyavin et al, 3'-Minor Groove Binder-DNA Probes Increase Sequence Specificity at PCR Extension Temperatures, Nucl Acids Res, Jan. 15, 2000, vol. 28, No. 2, pp. 655-661.
Tyagi et al, Molecular Beacons: Probes that Fluoresce Upon Hybridization, Nature Biotechnol, Mar. 1996, vol. 14, No. 3, pp. 303-308.
GenBank: ES210567.1.290382_2994_3970 Arabidopsis Ovule High Throughput cDNA Library Arabidopsis Thaliana cDNA, mRNA sequence, Dec. 30, 2007, online, retrieved on Apr. 16, 2013 from inernet: <URL:http://www.ncbi.nlm.nih.gov/nucest/ES210567>.
GenBank: GO976425.1. CCIG1779.131 CCIG Mimulus Guttatus DUN10 Fluoral Buds (H) Mimulus guttatus cDNA clone CCIG1779 5-, mRNA sequence, May 26, 2009, online, retrieved on Apr. 16, 2013 from interet: <URL:http://www.ncbi.nlm.nih.gov/nucest/G0976425>.
Johansson, Choosing Reporter-Quencher Pairs for Efficient Quenching Through Formation of Intramolecular Dimers 2 IN: Fluorescent Energy Transfer Nucleic Acid Probes: Designs and Protocols. 2006 Chapter 2, pp. 11-29.
Search Report, PCT/US13/28862, dated Jun. 10, 2013.
Dieffenbach, C. W., T. M. Lowe, and G. S. Dveksler. "General concepts for PCR primer design." PCR Methods Appl 3.3 (1993): S30-S37. http://img.dxycdn.com/trademd/upload/userfiles/file/2011/11/1322031004.pdf.
Rose, Timothy M., Jorja G. Henikoff, and Steven Henikoff. "CodeHop (COnsensus-DEgenerate hybrid oligonucleotide primer) PCR primer design." Nucleic Acids Research 31.13 (2003): 3763-3766. http://download.bioon.com/view/upload/201011/11/130022wqqmqqqm1mh1e1lw.attach.pdf.
Arvidsson, Samuel, et al. "QuantPrime—a flexible tool for reliable high-throughput primer design for quantitative PCR." BMC bioinformatics 9.1 (2008): 1. http://gene-quantification.net/arvidsson-et-al-quantprime-2008.pdf.
Tusnady, Gabor E., et al. "BiSearch: primer-design and search tool for PCR on bisulfite-treated genomes." Nucleic acids research 33.1 (2005): e9-e9. http://qpcrupdate.org/tusnady-bisearch-web-server.pdf.
Rychlik, Wojciech. OLIGO 7 primer analysis software. Humana Press, 2007. http://s3.amazonaws.com/academia.edu.documents/32125103/OLIGO_7_article.pdf?AWSAccessKeyId=AKIAJ56TQJRTWSMTNPEA&Expires=1467938443&Signature=QbG6JHc4%2FS98pCBXTeMsrEIOt7Y%3D&response-content-disposition=inline%3B%20filename%3DOligo_7_Primer_Analysis_Software.pdf.
SantaLucia, John. "Physical principles and visual-OMP software for optimal PCR design." PCR Primer Design (2007): 3-33. http://www.dnasoftware.com/wp-content/uploads/2015/08/7MythsofPCRChapter-1-1.pdf.
Dugat-Bony, Eric, et al. "HiSpOD: probe design for functional DNA microarrays." Bioinformatics 27.5 (2011): 641-648. http://bioinformatics.oxfordjournals.org/content/27/5/641.full.pdf+html.
Navin, Nicholas, et al. "Prober: oligonucleotide Fish probe design software." Bioinformatics 22.19 (2006): 2437-2438. http://citeseerx.ist.psu.edu/viewdoc/download?doi=10.1.1.103.4581&rep=rep1&type=pdf.
Shin, Soo-Yong, et al. "Multiobjective evolutionary optimization of DNA sequences for reliable DNA computing." IEEE Transactions on Evolutionary Computation 9.2 (2005): 143-158. https://www.researchgate.net/profile/Soo-Yong_Shin/publication/3418142_Multiobjective_evolutionary_optimization_of_DNA_sequences_for_reliable_DNA_computing/links/0046352ef98a81cf4b000000.pdf.
Feldkamp, Udo, Hilmar Rauhe, and Wolfgang Banzhaf. "Software tools for DNA sequence design." Genetic Programming and Evolvable Machines 4.2 (2003): 153-171. http://web.cs.mun.ca/~banzhaf/papers/softwaretools.pdf.
Shen, Zhiyong, et al. "MPprimer: a program for reliable multiplex PCR primer design." BMC bioinformatics 11.1 (2010): 1. https://www.semanticscholar.org/paper/MPprimer-a-program-for-reliable-multiplex-PCR-Shen-Qu/2f90b515df8e399df1cc040550aa226fdc7b8e2f/pdf.
Shin, Soo-Yong, In-Hee Lee, and Byoung-Tak Zhang. "Microarray probe design using ε -multi-objective evolutionary algorithms with thermodynamic criteria." Workshops on Applications of Evolutionary Computation. Springer Berlin Heidelberg, 2006. http://citeseerx.ist.psu.edu/viewdoc/download?doi=10.1.1.66.3111&rep=rep1&type=pdf.
Akio Kuroda, Tibor A. Rauch, Ivan Todorov, Hsun Teresa Ku, Ismail H. Al-Abdullah, Fouad Kandeel, Yoko Mullen, Gerd P. Pfeifer, Kevin Ferreri, "Insulin Gene Expression Is Regulated by DNA Methylation", PLoS One | www.plosone.org Sep. 1, 2009 | vol. 4 | Issue 9 | e6953.
Vishnu Swamp, M.R. Rajeswari, "Circulating (cell-free) nucleic acids—A promising, non-invasive tool for early detection of several human diseases", FEBS Letters 581 (2007) 795-799.
Rakyan VK, Beyan H, Down TA, Hawa MI, Maslau S, Aden D, Daunay A, Busato F, Mein CA, Manfras B, Dias KR, Bell CG, Tost J, Boehm BO, Beck S, Leslie RD. Identification of type 1 diabetes-associated DNA methylation variable positions that precede disease diagnosis. PLoS Genet. Sep. 2011; 7(9):e1002300. Epub Sep. 29, 2011.
Banerjee et al. A simple two-step protocol for the purification of human pancreatic beta cells. Diabetologia Apr. 1, 2009. vol. 52(4): 621-625.
Genbank Accession No. J00265.1—Human insulin gene, complete cds (GI: 186429, first submitted on Apr. 27, 1993 and updated Jan. 7, 2010, retrieved on Mar. 8, 2014 from http://www.ncbi.nlm.nih.gov/nuccore/J00265).
Bibikova et al. (2011a). High density DNA methylation array with single CpG site resolution. Genomics. Oct. 2011; 98 (4):288-95. Epub Aug. 2, 2011.
Lichtenstein AV, Melkonyan HS, Tomei LD, Umansky SR. Circulating nucleic acids and apoptosis. Ann N Y Acad Sci. Sep. 2001; 945:239-49. Review.
Campan M, Weisenberger DJ, Trinh B, Laird PW. MethyLight. Methods Mol Biol. 2009; 507:325-37.: a real-time PCR-based method to quantify DNA methylation at single specific cytosines. Methods Mol Biol. 2009; 507:281-301.
Swarup V, Rajeswari MR. Circulating (cell-free) nucleic acids—a promising, non-invasive tool for early detection of several human diseases. FEBS Lett. Mar. 6, 2007;581(5):795-9. Epub Feb. 2, 2007. Review.
Rani, S., M. Clynes & L. O'Driscoll. 2007. Detection of amplifiable mRNA extracellular to insulin producing cells: potential for predicting beta cell mass and function. Clin. Chem. 53: 1936-1944.
Christensen UB. EasyBeacons for the detection of methylation status of single CpG duplets. Methods Mol Biol. 2008; 129:137-60.
Li LC, Dahiya R. MethPrimer: designing primers for methylation PCRs. Bioinformatics. Nov. 2002; 18(11):1427-31.

(56) References Cited

OTHER PUBLICATIONS

Marras SA. Interactive fluorophore and quencher pairs for labeling fluorescent nucleic acid hybridization probes. Mol Biotechnol. Mar. 2008; 38(3):247-55. Epub Nov. 6, 2007.
Sosenko et al., A Risk Score for Type 1 Diabetes Derived From Autoantibody—Positive Participants in the Diabetes Prevention Trial-Type 1, Diabetes Care, 30:38-42, Mar. 2008.

* cited by examiner

METHOD FOR USING PROBE BASED PCR DETECTION TO MEASURE THE LEVELS OF CIRCULATING DEMETHYLATED BETA CELL DERIVED DNA AS A MEASURE OF BETA CELL LOSS IN DIABETES

CROSS-REFERENCE TO RELATED APPLICATION

The present application is a Continuation of U.S. patent application Ser. No. 13/784,017, filed Mar. 4, 2013, now U.S. Pat. No. 9,127,317, issued Sep. 8, 2015, which claims priority to U.S. Provisional patent Application No. 61/606,140, filed Mar. 2, 2012, and claims benefit of priority under 35 U.S.C. 371 from PCT/US13/288862 filed Mar. 4, 2013 (WO 2013/131083, published Sep. 6, 2013), entitled METHOD FOR USING PROBE BASED PCR DETECTION TO MEASURE THE LEVELS OF CIRCULATING DEMETHYLATED β CELL DERIVED DNA AS A MEASURE OF β CELL LOSS IN DIABETES, the entire content of which are incorporated by reference herein.

BACKGROUND OF THE INVENTION

Field

The present application relates to compositions and methods for assessing β cell loss by quantitating extrapancreatic demethylated β cell derived DNA with methylation status-specific oligonucleotide probes that target Polymerase Chain Reaction (PCR)-amplified DNA sequences of genes that are uniquely expressed by β cells.

The loss of insulin producing β cells results in glucose intolerance and the development of Type 1 (T1D) and Type 2 (T2D) diabetes. Eitan Akirav, Jake A. Kushner and Kevan C. Herold, "β-Cell Mass and Type 1 Diabetes Going, Going, Gone?", doi: 10.2337/db07-1817 Diabetes November 2008 vol. 57 no. 11 2883-2888. Currently, evaluation of β cell mass is carried out by measuring β cell products such as c-peptide. While useful, these measures do not provide real time information about active β cell loss.

There has thus been a long-felt need for a method capable of accurately evaluating β cell death so as to improve disease diagnosis, allow for disease staging, and provide a better evaluation of clinical treatment efficacy. There is further a great need in the art for compositions and methods for non-invasively monitoring β cell destruction in individuals having, or at risk of developing, diabetes mellitus ("diabetes"), including Type-1 and Type-2 Diabetes (T1D and T2D, respectively), as well as gestational diabetes.

Epigenetic modifications of DNA control cell-type specific gene expression. DNA methylation is one example of an epigenetic modification that affects gene. Methylation of DNA occurs at CpG dinucleotide sites, and this modification maintains a transcriptionally repressive chromatin configuration (Miranda et al., 2007, J. Cell Physiol. 213:384-390). Conversely, demethylation of CpG dinucleotide sites allows a transcriptionally permissive configuration (Id). Beta cells express insulin, and thus, maintain a transcriptionally-permissive hypomethylated regulatory region for the insulin gene (INS). Indeed, Genomic DNA sequences near the insulin gene are methylated in non-β cell cell types. Ley, Timothy J., et al. "DNA methylation and regulation of the human beta-globin-like genes in mouse erythroleukemia cells containing human chromosome 11." Proceedings of the National Academy of Sciences 81.21 (1984): 6618-6622.) Therefore, the presence of hypomethylated insulin gene DNA outside of the pancreas of a subject correlated with the release of hypomethylated insulin gene DNA from dead and dying (e.g., apoptotic) β cells. Id. and Kuroda A, Rauch T A, Todorov I, Ku H T, Al-Abdullah I H, et al. (2009) Insulin Gene Expression Is Regulated by DNA Methylation. PLoS ONE 4(9): e6953. doi:10.1371/journal.pone.0006953.

SUMMARY OF THE INVENTION

A method is provided for the detection of extrapancreatic circulating β cell-derived DNA that is indicative of acute and chronic β cell destruction, and thus provides an early biomarker for β cell death in human tissues, serum and other bodily fluids, such as saliva. The method can identify β cell death before the onset of hyperglycemia and diabetes. This strategy may prove useful for monitoring β cell destruction in individuals at risk for the development of diabetes, monitoring the progression of β cell destruction in individuals with diabetes, and use as a marker to guide therapy in patients with diabetes with possible ongoing β cell destruction.

In various embodiments, methods of the invention assesses the presence of β cell-derived DNA that is released upon β cell death by using a quantitative probe technology in a traditional PCR assay. By using probes, the method permits one to identify demethylated insulin DNA patterns that are present only in β cells. Therefore, the method provides a bioassay for detecting β cell loss in diabetes to provide a method capable of improving disease diagnosis, allowing for disease staging, and providing a better evaluation of clinical treatment efficacy. In various embodiments of the invention detects β cell loss associated with T1D, T2D, or gestational diabetes, or any combination thereof.

The method as disclosed herein uses a stepwise detection and analysis of β cell and non-β cell derived insulin DNA. The key principle behind the method is the existence of unique DNA methylation patterns in the β cells that are absent from other cells in the body. That is, the islet β cell DNA methylation pattern associated with the insulin gene is reasonably unique, and the level of islet β cell-origin insulin gene DNA in the serum and other body fluids is altered by islet β cell death or pathology.

By first conducting a bisulfate conversion of DNA extracted from a bodily fluid of an individual, it becomes possible to quantify the relative abundance of β cell insulin DNA in the circulation, and hence whether that individual is experiencing β cell loss.

A method is developed for detecting β cell death in vivo by amplifying regions of genes that: i) are expressed in β cells(e.g., INS); and ii) contain CpG methylation sites, and then measuring the proportion of β cell-derived DNA in the serum or other body fluids. Generally, by using probes that are specific for DNA methylation patterns in β cells, circulating copies of β cell-derived demethylated DNA are detected after bisulfite treatment and PCR amplification. See, Darst RP, Pardo CE, Ai L, Brown KD, Kladde MP; "Bisulfite sequencing of DNA", Curr Protoc Mol Biol. 2010 July; Chapter 7: Unit 7.9.1-17. doi: 10.1002/0471142727.mb0709s91; "Methylation Analysis by Bisulfite Sequencing: Chemistry, Products and Protocols from Applied Biosystems", tools•thermofisher•com/content/sfs/manuals/cms 039258/•pdf, www•methods•info/Methods/DNA methylation/Bisulphite sequencing•html each of which is expressly incorporated herein by reference. The method provides a noninvasive approach for detecting β cell death in vivo that may be used to track the progression of diabetes and guide its treatment.

It is likewise understood that specific other tissues and cell types may have distinct methylation patterns from other tissues, and therefore that a corresponding technique, using appropriate PCR primers and detection probes, may be used to detect apoptosis or other DNA release from these specific tissues or cell types into body fluids.

As an alternate to serum, saliva may also contain sufficient DNA containing epigenetic DNA modifications to provide a basis for diagnosis. During cell death most of the nuclear DNA is converted into nucleosomes and oligomers (Umansky, S. R., et al. [1982], "In vivo DNA degradation of thymocytes of gamma-irradiated or hydrocortisone-treated rats"; Biochim. Biophys. Acta 655:9-17), which are finally digested by macrophages or neighboring cells. However, a portion of this degraded DNA escapes phagocytic metabolism, and can be found in the bloodstream (Lichtenstein, A. V., et al. [2001], "Circulating nucleic acids and apoptosis"; Ann NY Acad Sci, 945:239-249), and also in bodily fluids. The present invention addresses the detection of beta cell-specific epigenetic modifications that are detectable in bodily fluids such as plasma and saliva following the destruction of beta cells.

A method is provided for the sensitive and specific detection of β cell death in vivo in models of autoimmune and chemically induced diabetes in mice, in human tissues, and in serum from patients with T1D and T2D. This assay identifies a specific methylation pattern in the β cell insulin DNA. This method provides a biomarker for detecting β cell loss in prediabetic mammals during progression of diabetes.

A preferred method thus comprises the following steps:

1) Serum/plasma, or other body fluid is collected and DNA is extracted and substantially purified. Serum is reasonably available and usable, but collection of saliva may be deemed less invasive.

2) Purified DNA is treated with bisulfite, whereupon the bisulfite converts demethylated cytosines to uracil while sparing the methylated cytosines (see en•wikipedia•org/wiki/Bisulfite sequencing and "Methylation Analysis by Bisulfite Sequencing: Chemistry, Products and Protocols from Applied Biosystems", Invitrogen Corp. (2007) tools•thermofisher•com/content/sfs/manuals/cms 039258•pdf, expressly incorporated herein by reference in their entirety; see also en•Wikipedia•org/wiki/DNA methylation expressly incorporated herein by reference)(other methylation-sensitive distinctions may be exploited to distinguished between methylated and demethylated DNA, as known in the art).

3) Circulating DNA exists in relatively low abundance. Therefore, bisulfite treated DNA is subject to a 1$^{st}$ step PCR. This reaction is methylation insensitive and is designed to increase the availability of DNA template. PCR products are run on a standard gel electrophoresis and purified. Since the DNA is previously bisulfate treated, there will be distinct DNA subpopulations corresponding to methylated and demethylated insulin gene DNA.

4) Purified DNA is used for a methylation sensitive reaction, that is, the reaction distinguishes between amplified DNA corresponding to methylated insulin gene DNA and demethylated insulin gene DNA (i.e., from β cells). The reaction uses methylation sensitive probes to detect and differentiate demethylated insulin DNA from β cell origin from methylated insulin DNA of non-β cell origin.

Optionally, relative numbers of β cell derived DNA are presented as "methylation index" or $2^{(methylated\ DNA-demethylated\ DNA)}$ or the difference between methylated DNA and demethylated DNA. Other quantitative analysis of the results, as well as historical trend analysis is possible. Further, the amount of β cell derived DNA may be normalized on a different basis than non-β cell derived DNA representing the insulin gene. For example, a tracer similar in characteristics to the β cell derived DNA (but unique with respect to endogenous DNA) may be quantitatively injected into a patient.

5) Provide a quantitative reference for the amount of β cell derived DNA normalized for dilution, degradation, secretion/excretion factors, etc.

It is therefore an object to provide a method for monitoring beta cell death, comprising: extracting and purifying DNA from a body fluid of an animal; treating the extracted purified DNA with bisulfite to convert demethylated cytosine to uracil while sparing the methylated cytosines; amplifying the bisulfite-treated DNA using polymerase chain reaction; purifying the amplified bisulfite-treated DNA; performing a methylation sensitive reaction on the purified bisulfite-treated DNA using at least two different methylation specific probes which quantitatively distinguish between demethylated insulin DNA of β cell origin and methylated insulin DNA of non-β cell origin; and computing a quantitative relationship between methylated insulin DNA and demethylated insulin DNA.

It is a further object to provide a method for monitoring cell death of a cell type having at least one DNA portion that has a unique DNA CpG methylation pattern as compared to other cells, which is released into body fluids upon cell death of cells of the cell type, comprising: extracting and purifying DNA that comprises the DNA portion; treating the extracted purified DNA with bisulfite to convert cytosine to uracil while sparing the CpG methylated cytosines; amplifying a region of the bisulfite-treated DNA that comprises the DNA portion by polymerase chain reaction using DNA CpG methylation pattern independent primers; determining a quantitative relationship between the DNA portion having the unique DNA CpG methylation pattern to the DNA portion lacking the unique DNA CpG methylation pattern, by employing the DNA CpG methylation pattern-specific probes; computing a difference between the DNA portion having the unique DNA CpG methylation pattern and the DNA portion lacking the unique DNA CpG methylation pattern.

Another object provides a method for monitoring beta cell death, comprising: extracting and purifying genomic DNA from a body fluid of an animal, wherein the genomic DNA comprises at least a portion of a gene that is predominantly expressed by β cells and that contains a CpG methylation site; treating the genomic DNA with bisulfite; performing a polymerase chain reaction (PCR) with primers that flank a region of the genomic DNA that comprises the CpG methylation site; purifying the PCR products; melting the PCR products into single strands; hybridizing the single-stranded PCR products with a first oligonucleotide probe capable of hybridizing with a target sequence that comprises a site corresponding to a bisulfite-converted CpG site and a second oligonucleotide probe capable of hybridizing with a target sequence that comprises a site corresponding to a bisulfite-nonconverted CpG site, and wherein the probes each comprise a non-FRET label pair consisting of a fluorophore and a quencher, and wherein interaction of the first oligopeptide probe or second oligopeptide probe with a respective target causes the first oligopeptide probe or second oligopeptide probe to change from a first conformation to a second conformation, thereby changing the distance between the fluorophore and quencher of said label pair, and wherein in only one conformation do the fluorophore and quencher interact sufficiently to quench the fluorescence of the fluorophore by a predetermined amount; quantitatively measuring fluorescent signals emitted by the first oligopeptide probe and the second oligopeptide probe; and reporting a quantitative relationship of the fluorescent signal emitted by the first oligopeptide probe and the second oligopeptide probe, indicative of the relative amount of β cell-derived DNA versus non-β cell-derived DNA.

It is also an object to provide a kit for detecting β cell-derived demethylated genomic DNA in a biological sample, wherein the kit comprises: PCR primers that flank a portion of a gene that is predominantly expressed by β cells and contains a CpG methylation site; a first oligonucleotide probe capable of hybridizing with a first target sequence on a PCR product made using the PCR primers, wherein the first target sequence corresponds to at least one bisulfite-converted CpG site of the portion of the gene; and a second oligonucleotide probe capable of hybridizing with a target sequence on a PCR product made using the PCR primers of the kit, wherein the target sequence corresponds to at least one bisulfite-nonconverted CpG site of the portion of the gene, wherein the first oligopeptide probe and the first oligopeptide probe each comprise label that allows selective quantitation of the first oligopeptide probe and the second oligopeptide probe. Each probe may comprise a label pair consisting of a fluorophore and a quencher, and wherein a binding interaction of the first oligopeptide probe with the first target sequence, and the second oligopeptide probe with the second target sequence, causes a change from a first conformation to a second conformation, thereby changing an interaction between the fluorophore and quencher of said label pair, and wherein in only one conformation of the first and second conformations do the labels interact sufficiently to quench the fluorescence of the fluorophore by at least 25 percent.

The probes may be conjugated to a fluorophore and/or a quencher. The fluorophore may be at least one of 6-carboxy fluorescein and tetrachlorofluorescein. The quencher may be tetramethylrhodamine. The probe may employ a fluorescent resonant energy transfer (FRET) interaction between the fluorophore and quencher, wherein the fluorophore and quencher are selectively separated in dependence on a binding of the probe to a respective target. The probe may also employ a non-FRET interaction between the fluorophore and quencher, wherein the fluorophore and quencher have an interaction based on a conformation of the probe, and in which the conformation is selectively dependent on a binding of the probe to a respective target.

The methylation sensitive reaction may comprises quantitatively determining a release of a fluorophore from a probe bound to the purified bisulfite-treated DNA.

The DNA portion having the unique DNA CpG methylation pattern may comprise an insulin gene from a pancreatic beta cell. The body fluid may be, for example, blood, blood plasma, blood serum, saliva, or tears.

DETAILED DESCRIPTION

Figure 1:
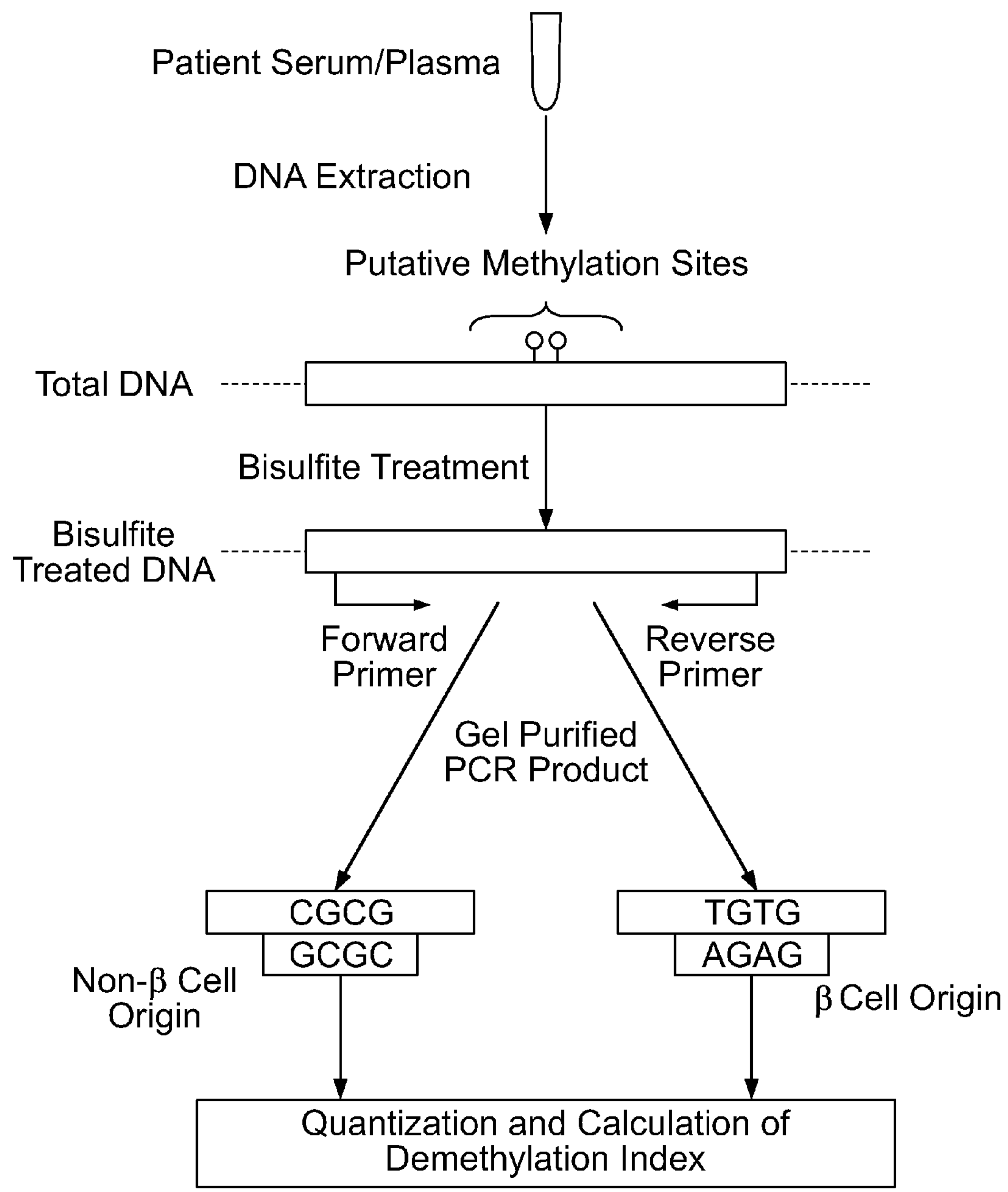
FIG. 1 sets forth the overall procedure for detecting circulating β cell DNA.

In various embodiments, the present technology substantially isolates nucleic acids from a sample of body fluid, for example blood plasma, saliva, spinal fluid, lymph fluid, synovial fluid, or tears, for example.

Various DNA extraction, isolation and purification technologies can be used, for example as taught in U.S. Pat. Nos. 4,935,342, 5,990,301, 6,020,124, 7,241,596, 6,485,903, 6,214,979, Re. 39,920 each of which is expressly incorporated herein by reference in its entirety.

An anion exchange material may be selected and employed which effectively adsorbs the target nucleic acids or protein complexes thereof. For example, commercially available anion exchange materials may be employed. Either strong or weak anion exchangers may be employed. A preferred weak exchanger can be one in which primary, secondary, or tertiary amine groups (i.e., protonatable amines) provide the exchange sites. The strong base anion exchanger has quaternary ammonium groups (i.e., not protonatable and always positively charged) as the exchange sites. Both exchangers can be selected in relation to their respective absorption and elution ionic strengths and/or pH for the nucleic acid being separated. Purification by anion exchange chromatography is described in U.S. Pat. No. 5,057,426 (see also EP 0 268 946 B1), expressly incorporated by reference herein in its entirety.

The material which is commercially available under the designation Q-Sepharose™ (GE Healthcare) is a particularly suitable. Q-Sepharose™, can be a strong anion exchanger based on a highly cross-linked, bead formed 6% agarose matrix, with a mean particle size of 90 μm. The Q-Sepharose™ can be stable in all commonly used aqueous buffers with the recommended pH of 2-12 and recommended working flow rate of 300-500 cm/h. In other preferred embodiments, the anion-exchange medium can be selected from sepharose-based quaternary ammonium anion exchange medium such as Q-filters or Q-resin.

The chromatographic support material for the anion charge used in the instant methods can be a modified porous inorganic material. As inorganic support materials, there may be used materials such as silica gel, diatomaceous earth, glass, aluminum oxides, titanium oxides, zirconium oxides, hydroxyapatite, and as organic support materials, such as dextran, agarose, acrylic amide, polystyrene resins, or copolymers of the monomeric building blocks of the polymers mentioned.

The nucleic acids can also be purified by anion exchange materials based on polystyrene/DVB, such as Poros 20 for medium pressure chromatography, Poros™ 50 HQ, of the firm of BioPerseptive, Cambridge, U.S.A., or over DEAE Sepharose™ DEAE Sephadex™ of the firm of Pharmacia, Sweden; DEAE Spherodex™, DEAE Spherosil™, of the firm of Biosepra, France.

A body fluid sample, such as blood plasma or saliva, containing nucleic acids or their proteinous complexes, is applied to the selected anion exchange material, and the nucleic acids or their complexes become adsorbed to the column material.

The contact and subsequent adsorption onto the resin can take place by simple mixing of the anion exchange media with the body fluid, with the optional addition of a solvent, buffer or other diluent, in a suitable sample container such as a glass or plastic tube, or vessel commonly used for handling biological specimens. This simple mixing referred to as batch processing, can be allowed to take place for a period of time sufficiently long enough to allow for binding of the nucleoprotein to the media, preferably 10 to 40 min. The media/complex can then be separated from the remainder of the sample/liquid by decanting, centrifugation, filtration or other mechanical means.

The anion exchange material can optionally be washed with an aqueous solution of a salt at which the nucleic acids remain bound to the anion exchange material, the washing being of sufficient volume and ionic strength to wash the non-binding or weakly binding components through the anion-exchange material. In some embodiments, the resin can be washed with 2×SSC (300 mM NaCl/30 mM sodium citrate (pH 7.0). Preferred ranges of the salt solutions are 300-600 nM NaCl/30 mM sodium citrate (pH 7.0). The resin may alternately be washed with 300-600 mM LiCl/10 mM NaOAc (pH 5.2).

The bound nucleic acids may then be eluted by passing an aqueous solution through the anion exchange material of increasing ionic strength to remove in succession proteins that are not bound or are weakly bound to the anion-exchange material and the nucleic acids of increasing molecular weight from the column. Both proteins and high and low molecular weight nucleic acids (as low as 10 base pairs) can be selectively eluted from the resin stepwise with the salt solution of concentrations from 300 mM to 2.0 M of NaCl and finally with 2.0 M guanidine isothiocyanate. LiCl solutions in the concentration range of 300 mM to 2.0 M of LiCl may also be used for stepwise elution.

The nucleic acids isolated may be in double-stranded or single-stranded form.

The body fluid can be pre-filtered through a membrane and supplemented with 10 mM EDTA (pH 8.0) and 10 mM Tris-HCL (pH 8.0) prior to adsorption onto the anion-exchange medium. Commercial sources for filtration devices include Pall-Filtron (Northborough, Mass.), Millipore (Bedford, Mass.), and Amicon (Danvers, Mass.). Filtration devices which may be used are, for example, a flat plate device, spiral wound cartridge, hollow fiber, tubular or single sheet device, open-channel device, etc.

The surface area of the filtration membrane used can depend on the amount of nucleic acid to be purified. The membrane may be of a low-binding material to minimize adsorptive losses and is preferably durable, cleanable, and chemically compatible with the buffers to be used. A number of suitable membranes are commercially available, including, e.g., cellulose acetate, polysulfone, polyethersulfone, and polyvinylidene difluoride. Preferably, the membrane material is polysulfone or polyethersulfone.

The body fluid, for example blood plasma or saliva, can be supplemented with EDTA and Tris-HCL buffer (pH 8.0) and digested with proteinases, such as for example Proteinase K, prior to adsorption onto the anion exchange medium.

The anion-exchange medium can be immobilized on an individualized carrier such as a column, cartridge or portable filtering system which can be used for transport or storage of the medium/nucleoprotein bound complex. The nucleic acid/anion exchange may be maintained in storage for up to 3 weeks.

A kit may be provided with a solid carrier capable of adsorbing the nucleic acids containing in a sample of a body fluid, for example blood plasma or saliva. The kit may also contain other components for example, reagents, in concentrated or final dilution form, chromatographic materials for the separation of the nucleic acids, aqueous solutions (buffers, optionally also in concentrated form for final adjusting by the user) or chromatographic materials for desalting nucleic acids which have been eluted with sodium chloride.

The kit may also contain additional materials for purifying nucleic acids, for example, inorganic and/or organic carriers and optionally solutions, excipients and/or accessories. Such agents are known and are commercially available. For solid phase nucleic acid isolation methods, many solid supports have been used including membrane filters, magnetic beads, metal oxides, and latex particles. Widely used solid supports include silica-based particles (see, e.g., U.S. Pub. Pat. App. 2007/0043216 (Bair Jr., et al.); U.S. Pat. No. 5,234,809 (Boom et al.); WO 95/01359 (Colpan et al.); U.S. Pat. No. 5,405,951 (Woodard); WO 95/02049 (Jones); WO 92/07863 (Qiagen GmbH), each of which is expressly incorporated herein by reference). Inorganic components of carriers may be, for example, porous or non-porous metal oxides or mixed metal oxides, e.g. aluminum oxide, titanium dioxide, iron oxide or zirconium dioxide, silica gels, materials based on glass, e.g. modified or unmodified glass particles or ground glass, quartz, zeolite or mixtures of one or more of the above-mentioned substances. On the other hand, the carrier may also contain organic ingredients which may be selected, for example, from latex particles optionally modified with functional groups, synthetic polymers such as polyethylene, polypropylene, polyvinylidene fluoride, particularly ultra high molecular polyethylene or HD-polyethylene, or mixtures of one or more of the above-mentioned substances.

In addition, the reagent kit may also contain excipients such as, for example, a protease such as proteinase K, or enzymes and other agents for manipulating nucleic acids, e.g. at least one amplification primer, and enzymes suitable for amplifying nucleic acids, e.g. DNase, a nucleic acid polymerase and/or at least one restriction endonuclease. Alternately, a commercial polymerase chain reaction kit may be used to amplify the DNA samples, as discussed below. DNA is subject to degradation by DNases present in bodily fluids, such as saliva. Thus, in certain embodiments, it is advantageous to inhibit DNase activity to prevent or reduce the degradation of DNA so that sufficiently large sequences are available for detection.

After collection, the sample may be treated using one or more methods of inhibiting DNase activity, such as use of ethylenediaminetetraacetic acid (EDTA), guanidine-HCl, GITC (Guanidine isothiocyanate), N-lauroylsarcosine, Na-dodecylsulphate (SDS), high salt concentration and heat inactivation of DNase.

After collection, the sample may be treated with an adsorbent that traps DNA, after which the adsorbent is removed from the sample, rinsed and treated to release the trapped DNA for detection and analysis. This not only isolates DNA from the sample, but, some adsorbents, such as Hybond™ N membranes (Amersham Pharmacia Biotech Ltd., Piscataway, N.J.) protect the DNA from degradation by DNase activity.

In some cases, the amount of DNA in a sample is limited. Therefore, for certain applications, sensitivity of detection may be increased by known methods.

Where DNA is present in minute amounts, larger samples can be collected and thereafter concentrated such as by butanol concentration or concentration using Sephadex™ G-25 (Pharmacia Biotech, Inc., Piscataway N.J.).

Once obtained, the bodily fluid derived DNA may be used as an alternate to serum-derived DNA as discussed below. Since the technology is ratiometric, it is dependent not on the absolute quantity of DNA available, but the proportional relationships of the methylated and unmethylated portions. In general, the disposition of these types in the various body fluids is not believed to be highly dependent on the fluid type, and calibration techniques can be used to account for persistent and predictable differences in the fluid methylated/unmethylated ratios.

Bisulfite Treatment

DNA from serum samples was purified using the Qiagen QIAamp DNA Blood Kit following the manufacturer-recommended protocol. Synthetic unmethylated and methylated DNA was purchased from Zymo research. DNA was then subjected to bisulfite treatment and purified on a DNA binding column to remove excessive bisulfite reagent using the Zymo EZ DNA Methylation Kit.

First-Step PCR and Gel Extraction.

A methylation-independent reaction was carried out to increase the DNA template for PCR analysis.

For the reaction, bisulfite-treated DNA template was added to Zymo Taq Premix. The amplification proceeded for, e.g., 50 cycles. The PCR products were excised from a 3% agarose gel. Negative controls without DNA did not yield products in the first-step reaction.

PCR products obtained using methylation-independent primers were purified using a Qiagen PCR Purification Kit.

Methylation-specific Analysis

Methylation-specific DNA probes are used for the detection of β cell derived DNA. These probes are able to quantitatively and sensitively detect circulation demethylated and methylated DNA from a β cell and a non-β cell origin, respectively. The new probes replace the previously published methylation specific primers (see Akirav E M, Lebastchi J, Galvan E M, Henegariu O, Akirav M, Ablamunits V, Lizardi P M, and Herold K C. Detection of β cell death in diabetes using differentially methylated circulating DNA. PNAS, 2011, Proceedings of the National Academy of Sciences, 2011, November: 108(19018-23), expressly incorporated herein by reference, hereinafter Akirav et al. (2011). See also Husseiny M I, Kuroda A, Kaye A N, Nair I, Kandeel F, et al. (2012) Development of a Quantitative Methylation-Specific Polymerase Chain Reaction Method for Monitoring Beta Cell Death in Type 1 Diabetes. PLoS ONE 7(10): e47942. doi:10.1371/journal.pone.0047942, expressly incorporated herein by reference), which presented with a relatively low specificity (i.e. demethylated primers detected methylated DNA and vice versa). Low specificity negatively impacts assay sensitivity by decrease detection limits of β cell derived demethylated DNA. Low DNA levels are presumably present during early β cell loss, such as prediabetes. See, U.S. Pat. No. 6,150,097, expressly incorporated herein by reference.

The overall procedure for the detection of circulating β cell DNA is depicted in FIG. 1. The steps leading to the use of probes are identical with those described in Akirav et al. (2011), which discloses the use of methylation-specific primers (and not probes) to detect β cell derived DNA. The primers were able to detect demethylated and methylated DNA from a β cell and a non-β cell origin, respectively. While useful, these primers had a relatively low specificity whereby demethylated primers detected methylated DNA and vice versa. Low specificity reduced assay sensitivity as it impaired the ability to detect very low levels of β cell-derived DNA, such as in the condition of early β cell loss and pre-diabetes.

DNA from serum samples was purified using the Qiagen QIAamp DNA Blood Kit following the manufacturer-recommended protocol. Synthetic unmethylated and methylated DNA was purchased from Millipore. Purified DNA was quantitated using a NanoDrop 2000 spectrophotometer. DNA was then subjected to bisulfite treatment and purified on a DNA binding column to remove excessive bisulfite reagent using the Zymo EZ DNA Methylation Kit.

The present method, in contrast, uses probe DNA that offers a significant improvement in sensitivity over the primers used in the prior art discussed above. That is, probe DNA allows for a highly specific recognition of two demethylated sites in the insulin gene. This tends to eliminate false positive readings and thus provides increased assay specificity and sensitivity. The following is used as probe for the detection of circulating DNA in the assay according to the present method:

A methylation-independent reaction was carried out to increase the DNA template for PCR analysis. For the reaction, bisulfite-treated DNA template was added to Zymo-Taq™ Premix (see, www•zymoresearch•com/protein/enzymes/zymotaq-dna-polymerase, expressly incorporated herein by reference.) The following PCR primers are used to amplify the human insulin position 2122220-2121985 on chromosome 11, GRCh37.p10, October 2012):

```
Forward primer:
                                    SEQ ID NO: 001
GTGCGGTTTATATTTGGTGGAAGTT

Reverse primer:
                                    SEQ ID NO: 002
ACAACAATAAACAATTAACTCACCCTACAA
```

Using the forward and reverse primers, PCR was conducted The PCR products were excised from a 3% agarose gel.

The PCR product (or amplicon) is detect by methylation status specific probes as follows:

a) Probes for the detection of methylated insulin DNA (i.e., DNA not derived from a β cell)(alternates):

```
                                    SEQ ID NO: 003
ACCTCCCGACGAATCT

                                    SEQ ID NO: 004
TACCTCTCGTCGAATCT
```

b) Probes for the detection of demethylated insulin DNA (i.e., DNA derived from a β cell)(alternates):

```
                                    SEQ ID NO: 005
ACCTCCCAACAAATCT
```

-continued

```
SEQ ID NO: 006
TACCTCCCATCAAATCT
```

In various embodiments, the methylation status-specific probes are conjugated with 6-carboxyfluorescein, abbreviated as FAM, thus permitting quantitative detection. See, en•wikipedia•org/wiki/TaqMan, expressly incorporated herein by reference. Other technologies may be used I conjunction with the present method; see, U.S. Pat. Nos. 6,103,476, 8,247,171, 8,211,644, 8,133,984, 8,093,003, 8,071,734, 7,972,786, 7,968,289, 7,892,741, 7,847,076, 7,842,811 7,803,528, 7,776,529, 7,662,550, 7,632,642, 7,619,059, 7,598,390, 7,422,852, 7,413,708, 7,399,591, 7,271,265, 7,241,596, 7,183,052, 7,153,654, 7,081,336, 7,070,933, 7,015,317, 7,005,265, 6,811,973, 6,680,377, 6,649,349, 6,548,254, 6,485,903, 6,485,901, each of which is expressly incorporated in its entirety. Probes may be Fluorescent Resonance Energy Transfer (FRET) or non-FRET type. See, U.S. Pat. No. 6,150,097, expressly incorporated herein by reference. U.S. Pat. No. 6,103,476 states: "The use of probes of this invention with interactive labels in assays for the identification of products of nucleic acid amplification reactions generally eliminates the need for post-amplification analysis to detect desired products and distinguish desired products from unwanted side reactions or background products. Of course, probes according to the invention can be added at the end of a synthesis process for end-point detection of products. In assays for monitoring the progress of an amplification reaction, the probes can be present during synthesis. The presence of probes improves the accuracy, precision and dynamic range of the estimates of the target nucleic acid concentration. Reactions in closed tubes may be monitored without ever opening the tubes. Therefore, assays using these probes with interactive labels can limit the number of false positives, because contamination can be limited."

c) PCR is done with an annealing temperature of 60° C. for 50 cycles and quantified using a Real Time PCR machine. A range of 52-65° C. for the PCR would be acceptable.

d) Values generated by demethylated probes are subtracted from values of methylated probes and a delta calculated.

Figure 2A:
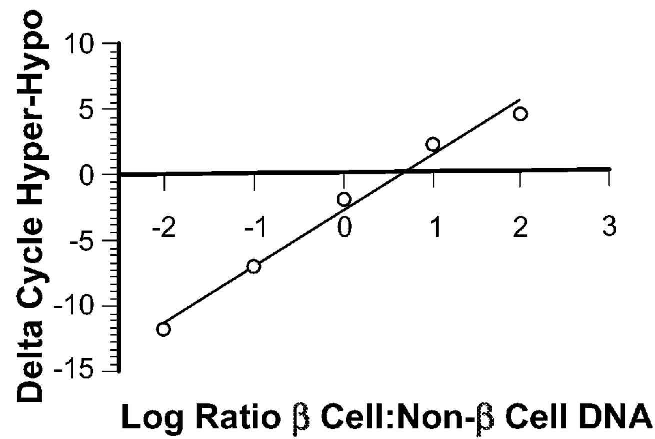
FIG. 2A shows the results of testing logarithmic serial dilutions of synthetic hypomethylated and hypermethylated DNA.
Figure 2B:
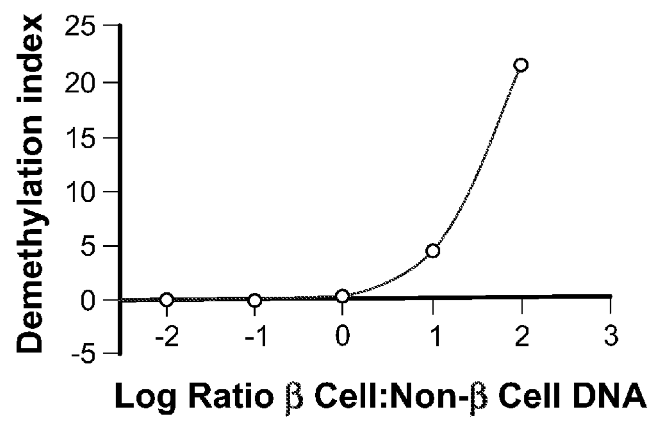
FIG. 2B shows that $\text{Log}_{10}$ transformation of demethylation index measurements show a non-linear fit.
Figure 2C:
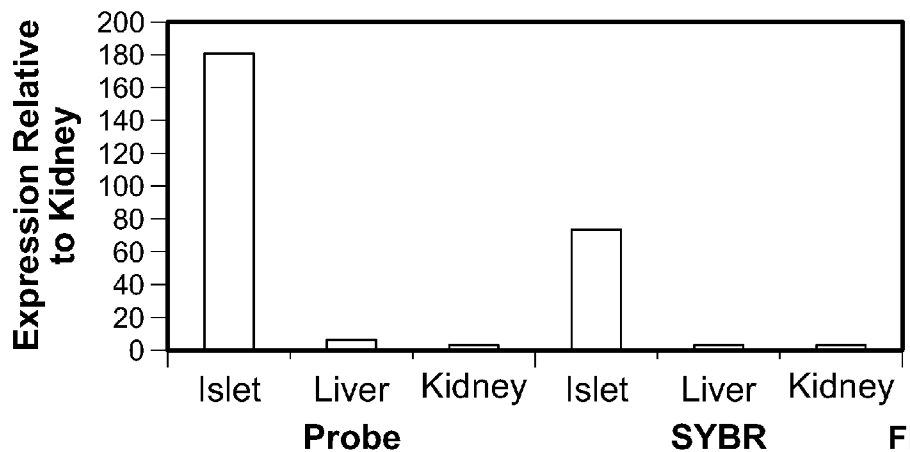
FIG. 2C shows the increase in specificity and sensitivity of the assay used in the present method.

Probe testing of logarithmic serial dilutions of synthetic hypomethylated and hypermethylated DNA has shown a linear behavior ($R^2$=0.98) of the delta between hypermethylated DNA and hypomethylated DNA (delta=hypermethylated DNA-hypomethylated DNA) over a wide range of DNA dilution (range is 4 log scale) see FIG. 2A. $Log_{10}$ transformation of demethylation index measures show a nonlinear fit ($R^2$=0.9999, DF 2) see FIG. 2B. FIG. 2C shows the specificity of the assay. The probe detects demethylated DNA at ~180 folds in islet (where β cells reside) compared with liver and kidney which do not express insulin. In contrast, primers detect the demethylated DNA at ~80 fold. In other words probes used according to an embodiment of the present invention are 2.25 times more specific than primers the primers used in accordance with Akirav et al. (2011).

Figure 3A:
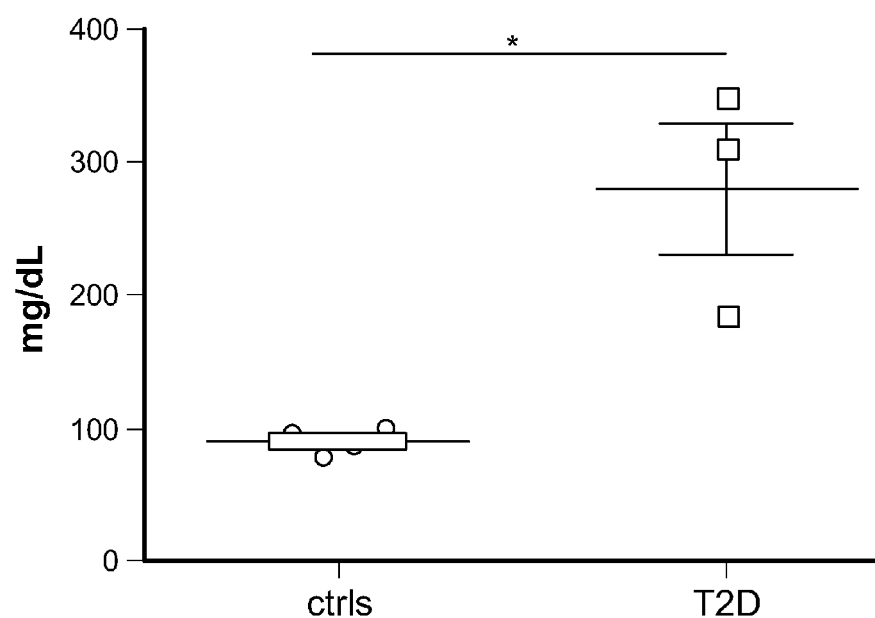
FIG. 3A demonstrates improved glucose levels in patients with long-standing Type 2 diabetes.
Figure 3B:
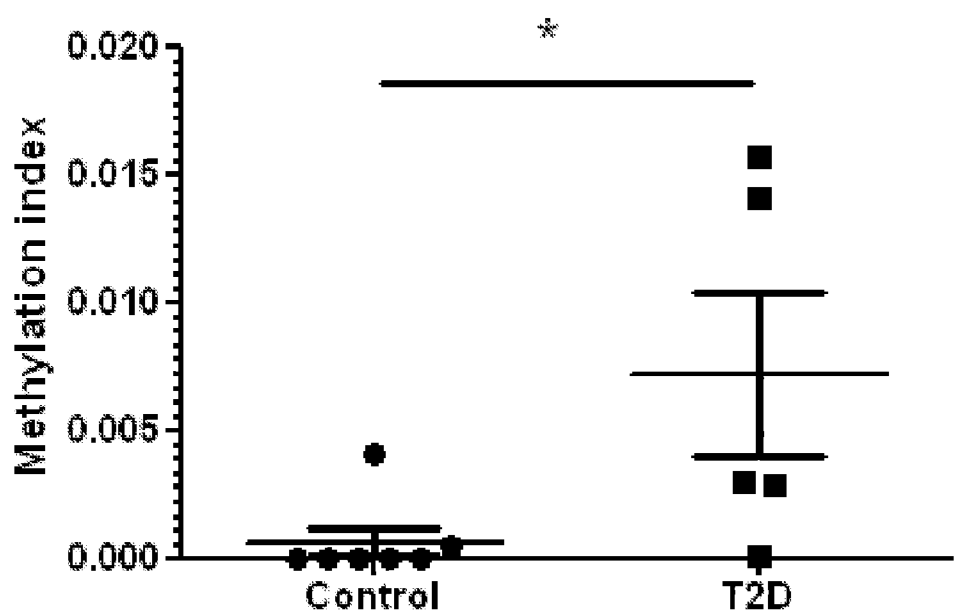
FIG. 3B shows that the probes according to the present technology reveal a significant increase in demethylated β cell DNA in the serum of the patients with long-standing Type 2 diabetes.
Figure 3C:
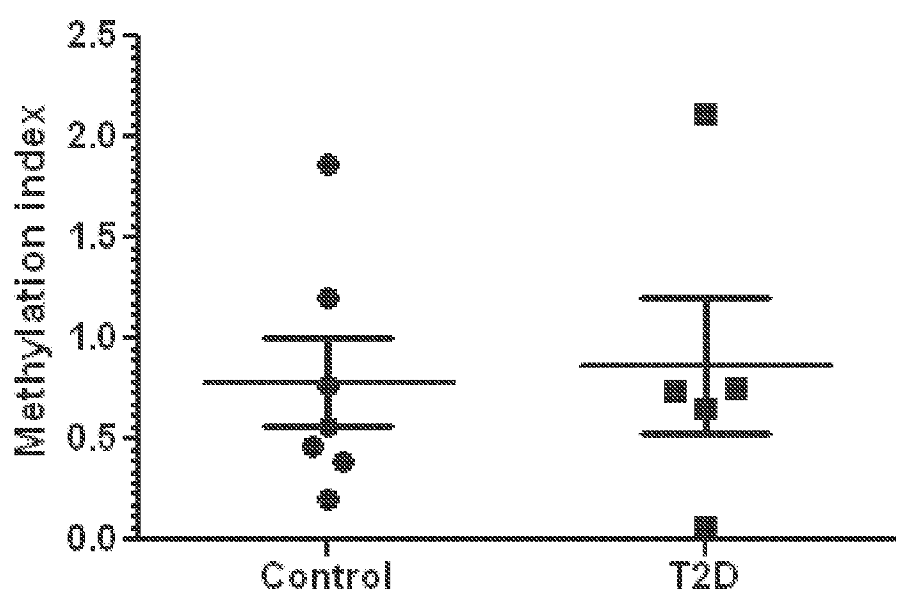
FIG. 3C shows that nested PCR using primers generally according to Akirav (2011) fail to reveal a significant increase in demethylated β cell DNA in the serum of the patients with long-standing Type 2 diabetes.

The present method extends the use of demethylated β cell derived DNA as a biomarker of Type 2 diabetes. The ability of the present assay to detect β cell loss in Type 2 diabetes is clearly shown by the experimental results obtained with the use of the present method. FIG. 3A shows impaired glucose levels in patients with long-standing Type 2 diabetes. FIG. 3B shows the increase in demethylated β cell DNA (i.e., increase in methylation index) in the serum of these patients, revealed as a significant difference (p=0.0286) from control by the use of the present probe technology. Similar results are also observed in animal models of Type 2 diabetes. FIG. 3C shows the use of primers from Akirav et al. (2011) to analyze the same sample set, and failed to detect any significant difference (p=0.87) in methylation index between control and T2D patients.

For PCR according to Akirav et al., (2011), shown in FIG. 3C was conducted for 40 cycles, with a melting temperature of 54° C., using primers as follows:

```
Forward primer:
                                    SEQ ID NO: 007
TTAGGGGTTTTAAGGTAGGGTATTTGGT

Reverse primer:
                                    SEQ ID NO: 008
ACCAAAAACAACAATAAACAATTAACTCACCCTACAA
```

The second step real-time methylation-specific nested PCR according to Akirav et al. (2011) was conducted with 50 cycles of amplification, and a melting temperature of 64° C., with the following primers:

```
Methylated forward primer:
                              SEQ ID NO: 009
GTGGATGCGTTTTTTGTTTTTGTTGGC

Methylated reverse primer:
                              SEQ ID NO: 010
CACCCTACAAATCCTCTACCTCCCG

Demethylated forward primer:
                              SEQ ID NO. 011
TTGTGGATGTGTTTTTTGTTTTTGTTGGT

Demethylated reverse primer:
                              SEQ ID NO: 012
CACCCTACAAATCCTCTACCTCCCA
```

Figure 4A:
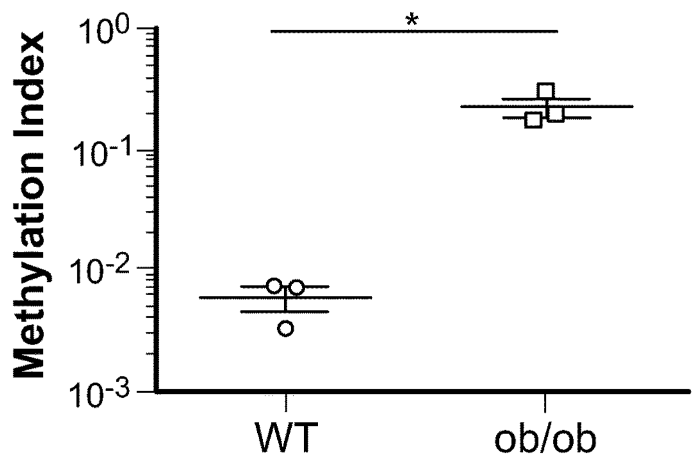
FIG. 4A shows the ability of the assay used in the present method to detect elevated demethylated DNA levels in the ob/ob leptin deficient mouse model of Type 2 diabetes.
Figure 4B:
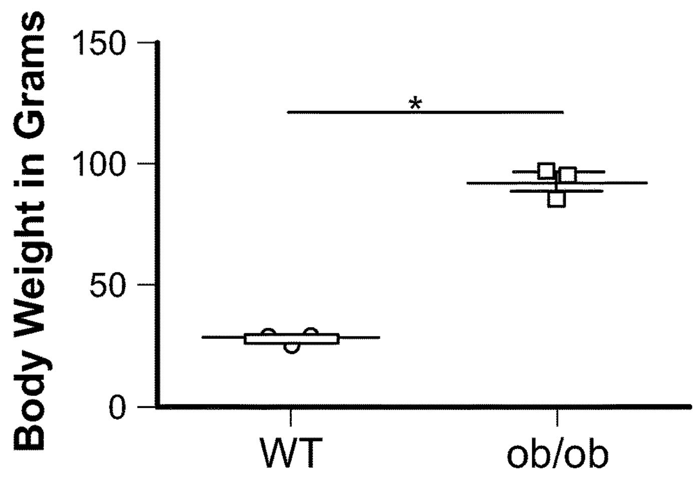
FIG. 4B correlates the levels shown in FIG. 4A with elevated body weight.
Figure 4C:
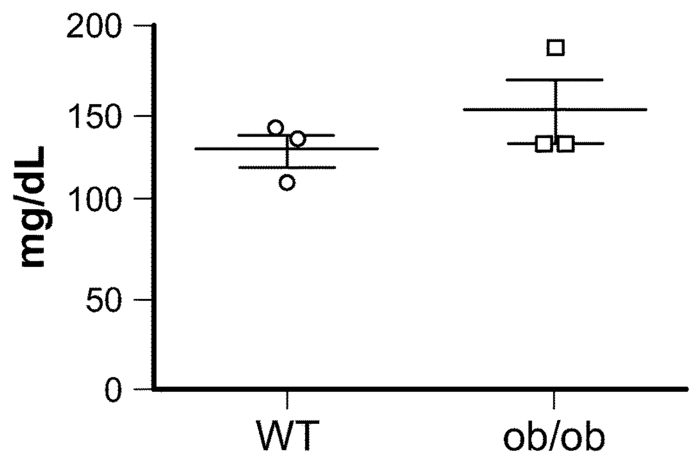
FIG. 4C correlates the levels shown in FIG. 4A with increased glucose levels.

FIG. 4A shows the ability of to detect elevated demethylated DNA levels in the ob/ob leptin deficient mouse model of type 2 diabetes. These levels were correlated with elevated body weight, shown in FIG. 4B, and increased glucose levels, shown in FIG. 4C.

Although the present invention has been described in relation to particular embodiments thereof, many other variations and modifications and other uses will become apparent to those skilled in the art. It is preferred, therefore, that the present invention be limited not by the specific disclosure herein, but only by the appended claim.

REFERENCES

Each of which is Expressly Incorporated Herein by Reference

1. Akirav E, Kushner J A, Herold K C (2008) β-cell mass and type 1 diabetes: Going, going, gone? Diabetes 57:2883-2888.
2. Bluestone J A, Herold K, Eisenbarth G (2010) Genetics, pathogenesis and clinical interventions in type 1 diabetes. Nature 464:1293-1300.
3. Waldron-Lynch F, Herold K C (2009) Advances in type 1 diabetes therapeutics: Immunomodulation and β-cell salvage. Endocrinol Metab Clin North Am 38:303-317.
4. Bougneres P F, et al. (1988) Factors associated with early remission of type I diabetes in children treated with cyclosporine. N Engl J Med 318:663-670.

5. Keymeulen B, et al. (2005) Insulin needs after CD3-antibody therapy in new-onset type 1 diabetes. N Engl J Med 352:2598-2608.
6. Ludvigsson J, Heding L (1982) Abnormal proinsulin/C-peptide ratio in juvenile diabetes. Acta Diabetol Lat 19:351-358.
7. Snorgaard O, Lassen L H, Binder C (1992) Homogeneity in pattern of decline of β-cell function in IDDM: Prospective study of 204 consecutive cases followed for 7.4 yr. Diabetes Care 15:1009-1013.
8. Greenbaum C J, et al.; Type 1 Diabetes Trial Net Research Group; European C-Peptide Trial Study Group (2008) Mixed-meal tolerance test versus glucagon stimulation test for the assessment of β-cell function in therapeutic trials in type 1 diabetes. Diabetes Care 31:1966-1971.
9. Steele C, et al. (2004) Insulin secretion in type 1 diabetes. Diabetes 53:426-433.
10. Erlich H, et al.; Type 1 Diabetes Genetics Consortium (2008) HLA DR-DQ haplotypes and genotypes and type 1 diabetes risk: Analysis of the Type 1 Diabetes Genetics Consortium families. Diabetes 57:1084-1092.
11. Hagopian W A, et al. (1995) Glutamate decarboxylase, insulin, and islet cell antibodies and HLA typing to detect diabetes in a general population-based study of Swedish children. J Clin Invest 95:1505-1511.
12. Verge C F, et al. (1996) Prediction of type I diabetes in first-degree relatives using a combination of insulin, GAD, and ICA512bdc/IA-2 autoantibodies. Diabetes 45: 926-933.
13. Shen J, Sosenko J, Skyler J S, Herold K C (2008) Prevention of type 1 diabetes: The time has come. Nat Clin Pract Endocrinol Metab 4:334-343.
14. Sosenko J M, et al.; Diabetes Prevention Trial Type 1 Study Group (2007) Increasing the accuracy of oral glucose tolerance testing and extending its application to individuals with normal glucose tolerance for the prediction of type 1 diabetes: The Diabetes Prevention Trial Type 1. Diabetes Care 30:38-42.
15. Medarova Z, Tsai S, Evgenov N, Santamaria P, Moore A (2008) In vivo imaging of a diabetogenic CD8+T cell response during type 1 diabetes progression. Magn Reson Med 59:712-720.
16. Klose R J, Bird A P (2006) Genomic DNA methylation: The mark and its mediators. Trends Biochem Sci 31:89-97.
17. Bartke T, et al. (2010) Nucleosome-interacting proteins regulated by DNA and histone methylation. Cell 143:470-484.
18. Wang G G, Allis C D, Chi P (2007) Chromatin remodeling and cancer, part II: ATP-dependent chromatin remodeling. Trends Mol Med 13:373-380.
19. Miranda T B, Jones P A (2007) DNA methylation: The nuts and bolts of repression. J Cell Physiol 213:384-390.
20. Grady W M, Rajput A, Lutterbaugh J D, Markowitz S D (2001) Detection of aberrantly methylated hMLH1 promoter DNA in the serum of patients with microsatellite un-stable colon cancer. Cancer Res 61:900-902.
21. Wallner M, et al. (2006) Methylation of serum DNA is an independent prognostic marker in colorectal cancer. Clin Cancer Res 12:7347-7352.
22. Muller H M, et al. (2003) DNA methylation in serum of breast cancer patients: An independent prognostic marker. Cancer Res 63:7641-7645.
23. Poitout V, et al. (1995) Morphological and functional characterization of β TC-6 cells: An insulin-secreting cell line derived from transgenic mice. Diabetes 44:306-313.
24. Sherry N A, et al. (2006) Effects of autoimmunity and immune therapy on β-cell turnover in type 1 diabetes. Diabetes 55:3238-3245.
25. Jayaraman S (2011) Assessment of beta cell viability. Curr Protoc Cytom 55:6.27.1-6.27.16.
26. Kuroda A, et al. (2009) Insulin gene expression is regulated by DNA methylation. PLoS ONE 4:e6953.
27. Giddings S J, King C D, Harman K W, Flood J F, Carnaghi L R (1994) Allele-specific inactivation of insulin 1 and 2 in the mouse yolk sac indicates imprinting. Nat Genet 6:310-313.
28. Leiter E H, et al. (2007) Unexpected functional consequences of xenogeneic transgene expression in β-cells of NOD mice. Diabetes Obes Metab 9 (Suppl 2):14-22.
29. Trudeau J D, et al. (2000) Neonatal β-cell apoptosis: A trigger for autoimmune diabetes? Diabetes 49:1-7.
30. Fujimoto K, et al. (2010) Loss of Nix in Pdx1-deficient mice prevents apoptotic and necrotic β cell death and diabetes. J Clin Invest 120:4031-4039.
31. Basadonna G, Montorsi F, Kakizaki K, Merrell R C (1988) Cyclosporin A and islet function. Am J Surg 156:191-193.
32. Berney T, et al. (2006) Detection of insulin mRNA in the peripheral blood after human islet transplantion predicts deterioration of metabolic control. Am J Transplant 6:1704-1711.
33. Best C H, Haist R E, Ridout J H (1939) Diet and the insulin content of pancreas. J Physiol 97:107-119.
34. Collins T J (2007) ImageJ for microscopy. Biotechniques 43 (Suppl 1):25-30.
35. Irina Botezatu, Ol'ga Serdyuk, Galina Potapova, Valery Shelepov, Raisa Alechina, Yuriy Molyaka, Vitaliy Anan'ev, Igor Bazin, August Garin, Mehti Narimanov, Vasiliy Knysh, Hovsep Melkonyan, Samuil Umansky, and Anatoly Lichtenstein (2000) "Genetic Analysis of DNA Excreted in Urine: A New Approach for Detecting Specific Genomic DNA Sequences from Cells Dying in an Organism", Clinical Chemistry 46:8 1078-1084.
36. Umansky, S. R., et al. (1982) "In vivo DNA degradation of thymocytes of gamma-irradiated or hydrocortisone-treated rats"; Biochim. Biophys. Acta 655:9-17.
37. Lichtenstein, A. V., et al. (2001), "Circulating nucleic acids and apoptosis"; Ann NY Acad Sci, 945:239-249.

SEQUENCE LISTING APPENDIX

```
<210> 1
<211> 25
<212> DNA
<213> Artificial Sequence
<220>
<223> Forward PCR Primer for insulin gene
<400> 1
gtgcggttta tatttggtgg aagtt                25

<210> 2
<211> 30
<212> DNA
<213> Artificial Sequence
<220>
<223> Reverse PCR primer for insulin gene
<400> 2
acaacaataa acaattaact caccctacaa           30

<210> 3
<211> 16
<212> DNA
```

-continued

SEQUENCE LISTING APPENDIX

```
<213> Artificial Sequence
<220>
<223> Probe for the detection of methylated
non-beta cell insulin DNA
<400> 3
acctcccgac gaatct                          16

<210> 4
<211> 17
<212> DNA
<213> Artificial Sequence
<220>
<223> Probe for the detection of methylated
non-beta cell insulin DNA
<400> 4
tacctctcgt cgaatct                         17

<210> 5
<211> 16
<212> DNA
<213> Artificial Sequence
<220>
<223> Probe for the detection of demethylated
beta cell insulin DNA
<400> 5
acctcccaac aaatct                          16

<210> 6
<211> 17
<212> DNA
<213> Artificial Sequence
<220>
<223> probe for the detection of demethylated
beta cell insulin dna
<400> 6
tacctcccat caaatct                         17

<210> 7
<211> 28
<212> DNA
<213> Artificial Sequence
<220>
<223> Outer Forward PCR primer for nested PCR
according to Akirav et
al. (2011)
<400> 7
ttaggggttt taaggtaggg tatttggt             28

<210> 8
<211> 37
<212> DNA
<213> Artificial Sequence
<220>
<223> Outer Reverse PCR primer for nested PCR
according to Akirav et
al. (2011)
<400> 8
accaaaaaca acaataaaca attaactcac cctacaa    37

<210> 9
<211> 27
<212> DNA
<213> Artificial Sequence
<220>
<223> Inner Methylated Forward PCR primer for
nested PCR according to
Akirav et al. (2011)
<400> 9
gtggatgcgt tttttgtttt tgttggc              27

<210> 10
<211> 25
<212> DNA
<213> Artificial Sequence
<220>
<223> Inner Methylated Reverse PCR primer for
nested PCR according to
Akirav et al. (2011)
<400> 10
caccctacaa atcctctacc tcccg                25

<210> 11
<211> 29
<212> DNA
<213> Artificial Sequence
<220>
<223> Inner Demethylated Forward PCR primer for
nested PCR according to
Akirav et al. (2011)
<400> 11
ttgtggatgt gtttttgtt tttgttggt             29

<210> 12
<211> 25
<212> DNA
<213> Artificial Sequence
<220>
<223> Inner Demethylated Reverse PCR primer for
nested PCR according to
Akirav et al. (2011)
<400> 12
caccctacaa atcctctacc tccca                25
```

SEQUENCE LISTING

```
<160> NUMBER OF SEQ ID NOS: 12

<210> SEQ ID NO 1
<211> LENGTH: 25
<212> TYPE: DNA
<213> ORGANISM: Artificial Sequence
<220> FEATURE:
<223> OTHER INFORMATION: Forward PCR Primer for insulin gene

<400> SEQUENCE: 1

gtgcggttta tatttggtgg aagtt                                      25


<210> SEQ ID NO 2
<211> LENGTH: 30
<212> TYPE: DNA
<213> ORGANISM: Artificial Sequence
<220> FEATURE:
```

<223> OTHER INFORMATION: Reverse PCR primer for insulin gene

<400> SEQUENCE: 2
acaacaataa acaattaact caccctacaa 30

<210> SEQ ID NO 3
<211> LENGTH: 16
<212> TYPE: DNA
<213> ORGANISM: Artificial Sequence
<220> FEATURE:
<223> OTHER INFORMATION: Probe for the detection of methylated non-beta cell insulin DNA

<400> SEQUENCE: 3
acctcccgac gaatct 16

<210> SEQ ID NO 4
<211> LENGTH: 17
<212> TYPE: DNA
<213> ORGANISM: Artificial Sequence
<220> FEATURE:
<223> OTHER INFORMATION: Probe for the detection of methylated non-beta cell insulin DNA

<400> SEQUENCE: 4
tacctctcgt cgaatct 17

<210> SEQ ID NO 5
<211> LENGTH: 16
<212> TYPE: DNA
<213> ORGANISM: Artificial Sequence
<220> FEATURE:
<223> OTHER INFORMATION: Probe for the detection of demethylated beta cell insulin DNA

<400> SEQUENCE: 5
acctcccaac aaatct 16

<210> SEQ ID NO 6
<211> LENGTH: 17
<212> TYPE: DNA
<213> ORGANISM: Artificial Sequence
<220> FEATURE:
<223> OTHER INFORMATION: probe for the detection of demethylated beta cell insulin dna

<400> SEQUENCE: 6
tacctcccat caaatct 17

<210> SEQ ID NO 7
<211> LENGTH: 28
<212> TYPE: DNA
<213> ORGANISM: Artificial Sequence
<220> FEATURE:
<223> OTHER INFORMATION: Outer Forward PCR primer for nested PCR according to Akirav et al. (2011)

<400> SEQUENCE: 7
ttaggggttt taaggtaggg tatttggt 28

<210> SEQ ID NO 8
<211> LENGTH: 37
<212> TYPE: DNA
<213> ORGANISM: Artificial Sequence
<220> FEATURE:
<223> OTHER INFORMATION: Outer Reverse PCR primer for nested PCR according to Akirav et al. (2011)

```
<400> SEQUENCE: 8

accaaaaaca acaataaaca attaactcac cctacaa                    37


<210> SEQ ID NO 9
<211> LENGTH: 27
<212> TYPE: DNA
<213> ORGANISM: Artificial Sequence
<220> FEATURE:
<223> OTHER INFORMATION: Inner Methylated Forward PCR primer for nested
      PCR according to Akirav et al. (2011)

<400> SEQUENCE: 9

gtggatgcgt tttttgtttt tgttggc                               27


<210> SEQ ID NO 10
<211> LENGTH: 25
<212> TYPE: DNA
<213> ORGANISM: Artificial Sequence
<220> FEATURE:
<223> OTHER INFORMATION: Inner Methylated Reverse PCR primer for nested
      PCR according to Akirav et al. (2011)

<400> SEQUENCE: 10

caccctacaa atcctctacc tcccg                                 25


<210> SEQ ID NO 11
<211> LENGTH: 29
<212> TYPE: DNA
<213> ORGANISM: Artificial Sequence
<220> FEATURE:
<223> OTHER INFORMATION: Inner Demethylated Forward PCR primer for
      nested PCR according to Akirav et al. (2011)

<400> SEQUENCE: 11

ttgtggatgt gttttttgtt tttgttggt                             29


<210> SEQ ID NO 12
<211> LENGTH: 25
<212> TYPE: DNA
<213> ORGANISM: Artificial Sequence
<220> FEATURE:
<223> OTHER INFORMATION: Inner Demethylated Reverse PCR primer for
      nested PCR according to Akirav et al. (2011)

<400> SEQUENCE: 12

caccctacaa atcctctacc tccca                                 25
```

What is claimed is:

1. A method, comprising:

receiving from an organism a sample of a circulating, excreted, or secreted body fluid, containing DNA, wherein the sample comprises DNA from apoptosis of pancreatic beta cells that give a cell-type-specific demethylation pattern, and DNA from other corresponding cells not having the cell-type-specific demethylation pattern;

treating the received DNA to distinguish between the DNA having the cell-type-specific demethylation pattern and the DNA not having the cell-type-specific demethylation pattern, to produce at least two different DNA products;

amplifying the at least two different DNA products in a quantitative manner by real-time PCR to produce at least two different amplified DNA products having a corresponding ratio of the DNA from cells having the cell-type-specific demethylation pattern to the other corresponding DNA from cells not having the cell-type-specific demethylation pattern;

selectively binding in a quantitative manner, during the real-time PCR, a plurality of different DNA oligonucleotide probes, each respective probe comprising a fluorophore and a quencher, to regions of the at least two different amplified DNA products which are respectively different dependent on the cell-type-specific demethylation pattern;

measuring optical properties of the plurality of different DNA oligonucleotide probes during the real-time PCR, dependent on a change in interaction between the fluorophore and the quencher due to the selectively binding; and determining, based on quantitative measurements of the measured properties of the plurality of different DNA oligonucleotide probes dependent on the selective binding to regions of the at least two different amplified DNA products, a ratio of the DNA from cells having an cell-type-specific demethylation pattern to the other corresponding DNA from cells not having the cell-type-specific demethylation pattern.

2. The method according to claim 1, wherein the sample is derived from at least one of blood plasma, saliva, spinal fluid, lymph fluid, synovial fluid, and tears.

3. The method according to claim 1, wherein the sample is a human sample derived from at least one of blood plasma, saliva, spinal fluid, lymph fluid, synovial fluid, and tears.

4. The method according to claim 1, wherein said treating the received DNA comprises purifying DNA contained in the sample and treating the purified DNA with bisulfite to convert demethylated cytosine to uracil while sparing the methylated cytosines.

5. The method according to claim 1, wherein the polymerase chain reaction is conducted using:

```
a forward primer:
                                SEQ ID NO: 001
GTGCGGTTTATATTTGGTGGAAGTT;
and

a reverse primer:
                                SEQ ID NO: 002
ACAACAATAAACAATTAACTCACCCTACAA.
```

6. The method according to claim 1, wherein the plurality of different DNA oligonucleotide probes is selected from the group consisting of:

```
                                SEQ ID NO: 003
ACCTCCCGACGAATCT;

                                SEQ ID NO: 004
TACCTCTCGTCGAATCT;

                                SEQ ID NO: 005
ACCTCCCAACAAATCT;
and

                                SEQ ID NO: 006
TACCTCCCATCAAATCT.
```

7. The method according to claim 1, wherein the plurality of different DNA oligonucleotide probes comprises:

a) at least one probe for detection of methylated insulin DNA of non-pancreatic beta cell origin selected from the group consisting of:

```
                                SEQ ID NO: 3
ACCTCCCGACGAATCT;
and

                                SEQ ID NO: 4
TACCTCTCGTCGAATCT;
and
```

b) at least one probe for detection of demethylated insulin DNA of pancreatic beta cell origin selected from the group consisting of:

```
                                SEQ ID NO: 005
ACCTCCCAACAAATCT;
and
```

-continued

```
                                SEQ ID NO: 006
TACCTCCCATCAAATCT.
```

8. A method, comprising:

receiving from a human a sample of a circulating, excreted, or secreted body fluid containing DNA, at least a portion of the DNA having a beta cell-specific demethylation pattern of an insulin gene, wherein the sample comprises DNA from the apoptosis of beta cells, and DNA from other cells;

extracting DNA from the sample;

treating the extracted DNA with bisulfite to distinguish between DNA having the beta cell specific demethylation pattern and DNA not having the beta cell specific demethylation pattern by converting demethylated cytosine of beta cells having the beta cell specific demethylation pattern to uracil while sparing methylated cytosines of non-beta cells not having the beta cell specific demethylation pattern;

amplifying the treated DNA products corresponding to the insulin gene, in a real-time polymerase chain reaction process using primers non-selective for the beta cell specific demethylation pattern, to produce at least two different amplified mixed DNA products having corresponding ratios to the treated DNA;

selectively hybridizing, in a quantitative manner, a plurality of different DNA oligonucleotide probes during the real-time PCR, each respective probe comprising a fluorophore and a quencher, having selectivity for distinguishing between amplified DNA products from the bisulfite-treated DNA having the beta cell specific demethylation pattern and amplified bisulfite-treated DNA products not having beta cell specific demethylation pattern;

measuring optical properties of the plurality of different DNA oligonucleotide probes during the real-time PCR, dependent on a change in interaction between the fluorophore and the quencher due to the selectively hybridizing; and determining, based on quantitative measurements of the measured properties of the plurality of different DNA oligonucleotide probes selectively hybridized to the amplified DNA products from the bisulfite-treated DNA, a ratio of the DNA from cells having the beta cell specific demethylation pattern to DNA from cells not having the beta cell specific demethylation pattern.

9. The method according to claim 8, wherein the sample is derived from at least one of blood plasma, saliva, spinal fluid, lymph fluid, synovial fluid, and tears.

10. The method according to claim 9, wherein the polymerase chain reaction is conducted using:

```
a forward primer:
                                SEQ ID NO: 001
GTGCGGTTTATATTTGGTGGAAGTT;
and

a reverse primer:
                                SEQ ID NO: 002
ACAACAATAAACAATTAACTCACCCTACAA;
and
```

wherein the plurality of different DNA oligonucleotide probes comprises:

a) at least one probe for detection of methylated insulin DNA of non-beta cell origin selected from the group consisting of:

SEQ ID NO: 3
ACCTCCCGACGAATCT;
and

SEQ ID NO: 4
TACCTCTCGTCGAATCT;
and b) at least one probe for detection of demethylated insulin DNA of beta cell origin selected from the group consisting of:

SEQ ID NO: 005
ACCTCCCAACAAATCT;
and

SEQ ID NO: 006
TACCTCCCATCAAATCT.

11. The method according to claim 8, wherein the plurality of different DNA oligonucleotide probes comprises:

a) at least one probe for detection of methylated insulin DNA of non-pancreatic beta cell origin selected from the group consisting of:

SEQ ID NO: 003
ACCTCCCGACGAATCT;
and

SEQ ID NO: 004
TACCTCTCGTCGAATCT;
and b) at least one probe for detection of demethylated insulin DNA of pancreatic beta cell origin selected from the group consisting of:

SEQ ID NO: 005
ACCTCCCAACAAATCT;
and

SEQ ID NO: 006
TACCTCCCATCAAATCT;

and provides a linear relationship between the log ratio of insulin gene DNA of pancreatic beta cell and insulin gene DNA of non-pancreatic beta cell origin with an $r^2$=0.98, for DNA samples having a demethylation index for insulin gene DNA between 100:1 and 1:100; and the plurality of different DNA oligonucleotide probes provides a detection of DNA from cells having the cell-type-specific demethylation pattern from pancreatic beta cells subject to 180 fold higher dilution than from liver or kidney cells.

* * * * *